(12) United States Patent
Wilson

(10) Patent No.: US 7,691,354 B2
(45) Date of Patent: Apr. 6, 2010

(54) SYNTHESIS OF SAPO-34 WITH ESSENTIALLY PURE CHA FRAMEWORK

(75) Inventor: Stephen T. Wilson, Libertyville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/503,467

(22) Filed: Jul. 15, 2009

(65) Prior Publication Data

US 2009/0275790 A1    Nov. 5, 2009

Related U.S. Application Data

(62) Division of application No. 11/157,102, filed on Jun. 20, 2005, now Pat. No. 7,578,987.

(51) Int. Cl.
| | |
|---|---|
| *C01B 39/54* | (2006.01) |
| *C01B 37/06* | (2006.01) |
| *C01B 37/08* | (2006.01) |
| *B01J 29/84* | (2006.01) |
| *B01J 29/85* | (2006.01) |
| *C07C 9/00* | (2006.01) |
| *C07C 9/06* | (2006.01) |
| *C07C 1/24* | (2006.01) |

(52) U.S. Cl. .................. 423/306; 423/DIG. 30; 502/60; 585/640; 585/800

(58) Field of Classification Search .............. 423/306, 423/702, 703, 704, 705, 706, 707, 708, DIG. 30; 585/640, 800; 502/60
See application file for complete search history.

(56) References Cited

U.S. PATENT DOCUMENTS

| | | | | |
|---|---|---|---|---|
| 4,076,796 A | * | 2/1978 | Reh et al. | 423/659 |
| 4,440,871 A | * | 4/1984 | Lok et al. | 502/214 |
| 4,786,487 A | * | 11/1988 | Kuehl | 423/306 |
| 5,096,684 A | * | 3/1992 | Guth et al. | 423/705 |
| 5,932,512 A | * | 8/1999 | Sun | 502/214 |
| 6,001,328 A | * | 12/1999 | Lillerud et al. | 423/718 |
| 6,166,282 A | * | 12/2000 | Miller | 585/638 |
| 6,287,522 B1 | * | 9/2001 | Lomas | 422/144 |
| 6,767,858 B1 | * | 7/2004 | Cao et al. | 502/214 |
| 7,578,987 B2 | * | 8/2009 | Wilson | 423/306 |

OTHER PUBLICATIONS

Yna Xu et al, "The Synthesis of SAPO-34 and CoSAPO-34 from a Triethylamine-Hyudrofluoric Acid-Water System", 1990, 86(2), 425-429.*

* cited by examiner

*Primary Examiner*—David M Brunsman
(74) *Attorney, Agent, or Firm*—Arthur E Gooding

(57) ABSTRACT

A process for producing an ElAPO molecular sieve with essentially pure CHA framework is disclosed. When El is silicon the process allows for a broad range of silicon content, and produces a catalyst with a high selectivity for the conversion of methanol to olefins.

6 Claims, 2 Drawing Sheets

SYNTHESIS OF SAPO-34 WITH ESSENTIALLY PURE CHA FRAMEWORK

CROSS-REFERENCE TO RELATED APPLICATION

This application is a Division of prior copending application Ser. No. 11/157,102 which was filed Jun. 20, 2005, now allowed, the contents of which are incorporated herein by reference thereto.

FIELD OF THE INVENTION

This invention relates to the synthesis of a catalyst and the use of this catalyst for the processing of oxygenates to low molecular weight olefins. More specifically, the catalyst has an essentially pure CHA framework over a wide range of silicon content, and is an enhanced catalyst for use in converting oxygenates to light olefins.

BACKGROUND OF THE INVENTION

Light olefins are an important basic chemical feedstock for the production of many plastics used in a variety of industries. Olefins are most commonly produced from petroleum feedstocks through the cracking of larger hydrocarbon molecules. The cracking process is either a catalytic or steam cracking process, and produces light olefins which consist primarily of ethylene and propylene.

An alternate source of light olefins is from the conversion of oxygenates to olefins. The primary oxygenate that is converted to an olefin is methanol. The preferred process is generally referred to as methanol-to-olefins (MTO) process. The primary olefins produced from this process are ethylene and propylene, and the process is performed over a catalytic molecular sieve. The MTO process enables an important alternative to petroleum sources of feeds for the production of light olefins. The sources of oxygenates include alcohols, such as methanol and ethanol; ethers, such as dimethyl ether and diethyl ether; and other oxygenates, such as methyl formate and dimethyl carbonate. These oxygenates can be produced from natural gas, fermentation of biomass, municipal wastes, and recycled organic materials. An important commercial consideration is that methanol can be readily produced from natural gas, or coal, and is easier and safer to handle and transport then either natural gas or coal.

There are many studies of molecular sieves for the use in methanol to olefin processes, with SAPO-34 disclosed as a preferred molecular sieve. In trying to improve the characteristics of SAPO-34, the molecular sieve has been subjected to various treatments. For example U.S. Pat. No. 5,932,512 discloses that the molecular sieve is synthesized and then treated with a fluoride compound to form a fluorinated silico-aluminophosphate molecular sieve. While there is some improvement in the total selectivity of ethylene plus propylene, there is also a shift in favor of greater ethylene selectivity and lower propylene selectivity. It is important to note that the '512 patent deals with a method of treating an already formed molecular sieve and loading it with fluoride, rather than producing the desired molecular sieve from a synthesis reaction mixture.

In searching for improved SAPO-34 catalysts, Y. Xu, et al., J. Chem. Soc. Faraday Trans. 86(2), 425-429 (1990) studied the effect of hydrofluoric acid (HF) on crystal growth, but found that the presence of HF favors the formation fewer and larger crystals. In addition, Xu et al., used higher concentration of the organic templating agent. The use of a fluoride source is known and discussed in the production of molecular sieves. U.S. Pat. No. 4,786,487 uses a fluoride source, but for the generation of sodalite and SAPO-20 which has an SOD framework type. Different types of molecular sieves are produced under different conditions, and there is no guidance as to the applicability of this to other molecular sieves. However, in the formation of catalyst for use in oxygenates to olefins it is preferred to form smaller crystals as larger crystals reduce the efficiency and shorten the regeneration cycle of the catalyst.

The preparation of a silicoaluminophosphate composition with a CHA framework structure in the presence of fluoride is reported in the PhD dissertation of Erling Halvorsen (K.-P. Lillerud, thesis advisor; University of Oslo, Department of Chemistry, 1996). This material is designated UiO-S4. In this work the authors claim that the preparation of pure UiO-S4 requires a TEAOH/$Al_2O_3$ ratio of 2 and low to medium HF content (HF/$Al_2O_3$=0.15-0.7). At lower TEAOH levels, mixtures of SAPO-5, SAPO-34, UiO-S6, and UiO-S4 were formed. For pure UiO-S4 the gel composition 2.0 TEAOH.1.0 $Al_2O_3$.1.0 $P_2O_5$.0.1 $SiO_2$.0.2 HF.50 $H_2O$ was digested at 150° C. for 21 hours. Halvorsen indicated that the XRD pattern of the as-synthesized product did not resemble the pattern of SAPO-34 much, but upon calcination the familiar pattern of SAPO-34 is observed. Elemental analysis of the product showed (mole fraction, normalized) P 0.461, Al 0.499, Si 0.032, F 0.08. The average crystallite size was approximately 1.0 micrometer. While presenting new materials, including the production of SAPO-34 in a mixture of materials, there was no testing for use in the MTO process.

The synthesis of SAPO-34 with TEAOH and HF is shown in U.S. Pat. No. 5,096,684. Example 10 uses gel composition 1.0 TEAOH.0.6 $SiO_2$.1.5 $Al_2O_3$.0.7 $P_2O_5$.100$H_2O$.1.0 HF and SEM analysis of the product shows nearly cubic crystals 2-15 μm in size, and a composition of $Si_{0.13}Al_{0.49}P_{0.38}$. Example 11 uses gel composition 1.0 TEAOH.1.00 $SiO_2$.1.75 $Al_2O_3$.0.75 $P_2O_5$.100$H_2O$.1.0 HF and produces a product with composition $Si_{0.12}Al_{0.50}P_{0.38}$. These preps are characterized by high $SiO_2$ levels in the reaction media and generate large crystals for the products.

A method of synthesizing aluminophosphate and silicoaluminophosphate molecular sieves and in particular to the synthesis of aluminophosphate and silicoaluminophosphate molecular sieves using N-methylethanolamine (MEA) as template with or without a source of fluoride is described in U.S. Pat. No. 6,767,858 B1. In example 1 the use of N-methyl ethanolamine as sole template results in good quality SAPO of CHA framework type but with 1.94 Si/CHA cage (16 mol % Si). In example 2, by combining TEACl with the MEA, SAPO with 0.96 Si/CHA cage (8 mol % Si) was produced. Alternatively, in example 3, by incorporating a F-source with the MEA, a SAPO molecular sieve of CHA framework type with an even lower level of silicon, 0.31 Si/CHA cage (2.5 mol % Si) was prepared. In all cases, no indication of crystal size or particle size was given. In the later case the equimolar Al and P content suggested that the acid site density would be very low which will produce a poor MTO catalyst, and not be an improvement.

The current state of production of a suitable SAPO-34 is still fraught with problems such as the generation of intergrowths in the crystals that results in crystals with a structure that has part CHA framework type and part AEI framework type, or the production of crystals that are too large. The mixture of framework types in the catalyst lowers the selectivity, and crystals that are too large rapidly coke up and have reduced activity in the process of methanol to olefin conversion.

SUMMARY OF THE INVENTION

The present invention is an improved process for the production of molecular sieve for use in methanol to olefin production. The process produces a metallo-aluminophosphate molecular sieve with an essentially pure CHA framework structure. The process comprises providing a reaction mixture having aluminum, phosphorous, water, an element El, an organic template, and a fluoride source. The mixture has a template to phosphorus ratio on a molar basis of less than 1. The mixture is crystallized at temperatures between about 100° C. and about 250° C. to form a catalyst after calcination having a chemical composition expressed on an anhydrous basis with an empirical formula of $(El_xAl_yP_z)O_2$, wherein "x" is the mole fraction of El and has a value from 0.001 to about 0.5, "y" is the mole fraction of Al and has a value of at least 0.01, "z" is the mole fraction of P and has a value of at least 0.01 and x+y+z=1. This molecular sieve has an essentially pure chabazite structure. El is an element selected from the group consisting of silicon, magnesium, zinc, iron, cobalt, nickel, manganese, chromium, and mixtures thereof. The molecular sieve is calcined in air to remove occluded organic template and fluoride.

Additional objects, embodiments and details of this invention can be obtained from the following drawings and detailed description of the invention.

DETAILED DESCRIPTION OF THE INVENTION

Figure 1:
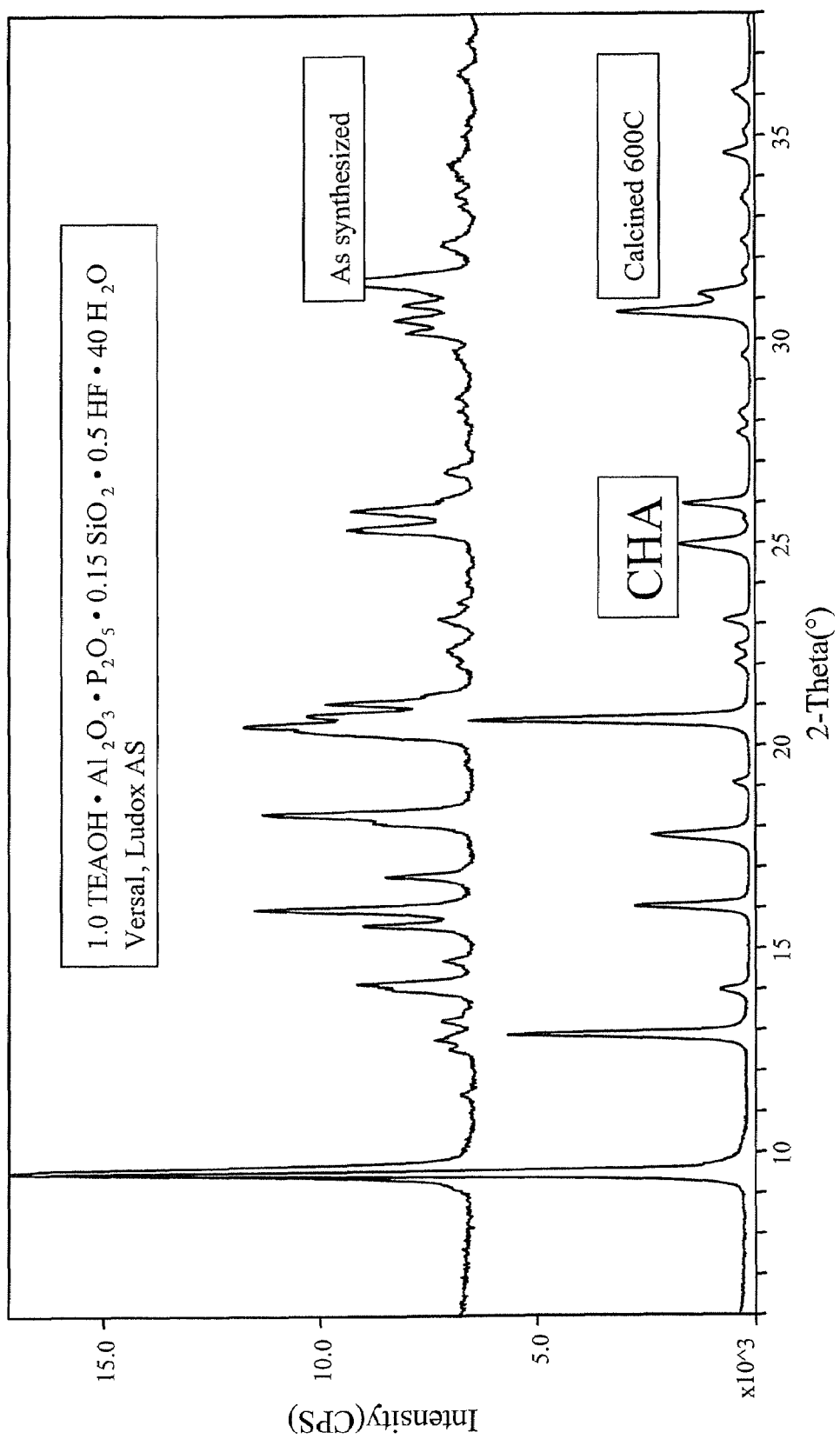
FIG. 1 is a comparison of XRD patterns of as synthesized and calcined F-SAPO-34 showing significant change in symmetry upon removal of fluoride and residual organic material.
Figure 2:
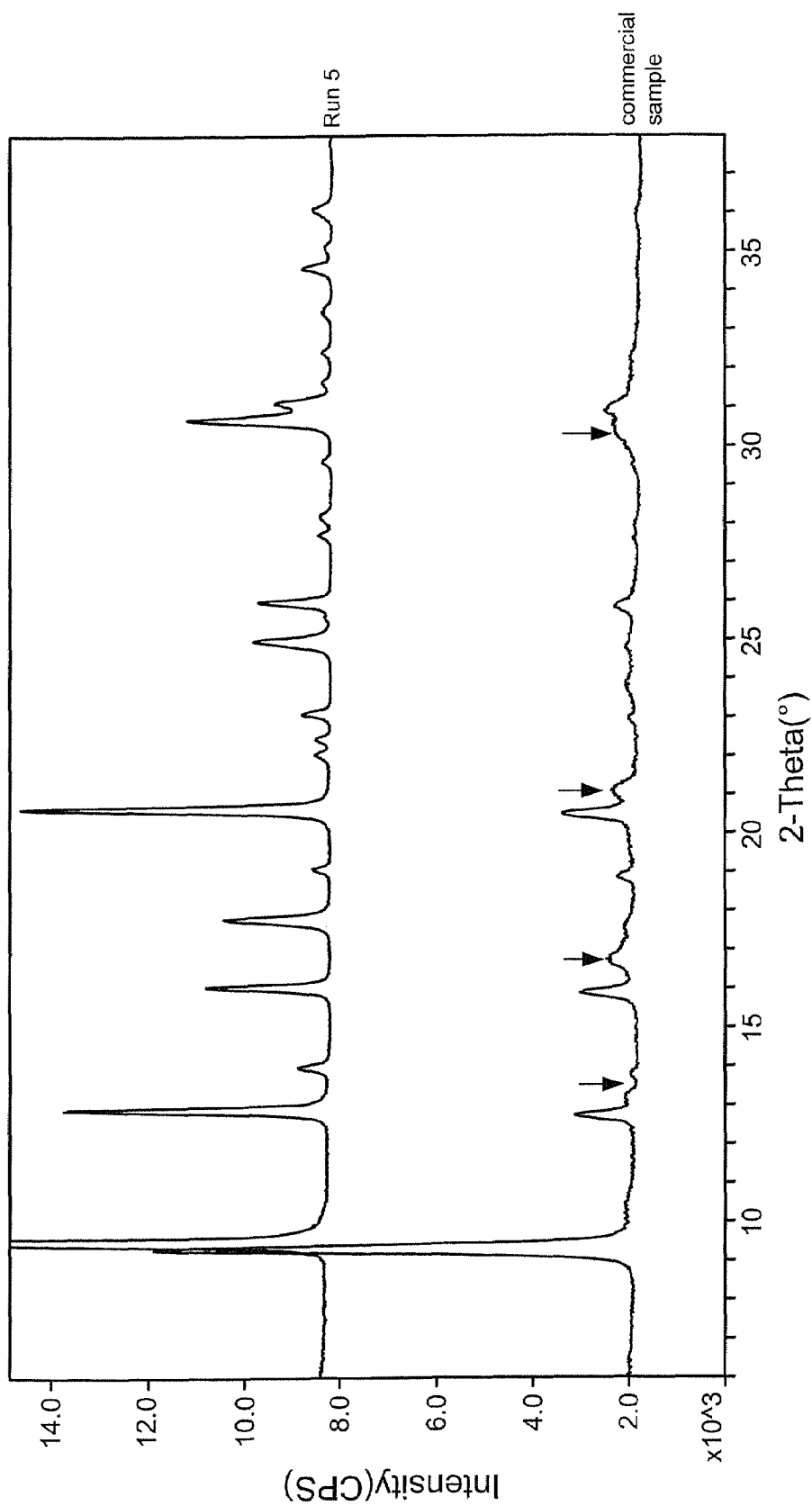
FIG. 2 is a comparison of XRD patterns of a calcined F-SAPO-34 and a commercial sample of SAPO-34 reference materials with a significant level of CHA/AEI intergrowths (arrows).

Molecular sieve catalysts are important for many hydrocarbon processes. One such process is the conversion of oxygenates to olefins, and in particular methanol to low molecular weight olefins, commonly referred to as MTO (methanol to olefins). The quality of the molecular sieve can affect the total conversion and selectivity of oxygenates to olefins. In forming an appropriate molecular sieve catalyst for MTO processes, similar molecular sieves can form in the same batch with one or more being preferred and others being undesired.

A molecular sieve that is used in the MTO process is a silico-aluminophosphate, or SAPO. SAPOs are molecular sieves with a microporous framework structure of $SiO_2$, $AlO_2$, and $PO_2$ tetrahedral oxide units. The performance of small pore SAPO molecular sieves in the catalytic conversion of methanol to small olefins depends on, but is not limited to, framework type, crystal size, crystal morphology, acid site density, and framework silicon (Si) content.

The invention is a process for the preparation of a molecular sieve catalyst for use in the conversion of oxygenates to olefins. The process comprises providing a reaction mixture having an aluminum source, a phosphorus source, an El source, water, an organic template source and a fluoride compound source. El is one or more elements chosen from silicon, magnesium, zinc, iron, cobalt, nickel, manganese, and chromium. A preferred source of silicon is fumed, colloidal, or precipitated silica. Preferred reactive sources of aluminum and phosphorus are pseudo-boehmite alumina and phosphoric acid, but organic phosphates or crystalline or amorphous aluminophosphates have been found satisfactory. A preferred source of fluoride is hydrofluoric acid (HF) with preferred amounts of fluoride in the reaction mixture at less than about 0.25 times the amount of phosphorus on a molar basis. Sources for elements "El" include oxides, hydroxides, alkoxides, nitrates, sulfates, halides, carboxylates, and mixtures thereof. Templating agents are amines and quaternary ammonium compounds, which include, but are not limited to tetraethyl ammonium hydroxide, tetraethyl ammonium phosphate, tetraethyl ammonium fluoride, tetraethyl ammonium bromide, tetraethyl ammonium chloride, tetraethyl ammonium acetate, dipropylamine (DPA), isopropylamine, cyclohexylamine, methylbutylamine, diethanolamine, and morpholine. Preferred templating agents include tetraethylammonium hydroxide, and morpholine. Templating agents are supplied to the reaction mixture in a ratio from 0.5 to 4 times the amount of aluminum on a molar basis. The template and phosphorus are supplied to the mixture at a ratio, on a molar basis, of less than or equal to about 1.

An optional component of the reaction mixture is seeds of the desired molecular sieve. Normally, to reduce the amount of intergrowths, it is necessary to use seed crystals with higher silicon content than that which is in the desired molecular sieve. The presence of small amounts of fluoride allows for the use of seed crystals with lower silicon content.

The reaction mixture is now placed in a sealed pressure vessel, optionally lined with an inert plastic material such as polytetrafluoroethylene and heated preferably under autogenous pressure at a temperature between about 50° and 250° C., preferably between about 100° and 200° C., and most preferably between about 150° and 200° C. for a time sufficient to produce crystals of the molecular sieve. Typically, the time varies from about 1 to about 120 hours and preferably from about 24 to about 48 hours. The desired product is recovered by any convenient method such as centrifugation, filtration or decanting.

After crystallization, the molecular sieve is calcined in air at a temperature of about 500 to about 700° C., preferably 600 to 650° C., for a time sufficient to substantially remove the fluoride and any occluded organic compounds. The calcining leaves the molecular sieve essentially fluoride free. This allows the molecular sieve framework to relax to the more symmetrical hexagonal unit cell that is typical of the CHA framework type.

The molecular sieve formed has a chemical composition on an anhydrous basis after calcination that can be expressed by an empirical formula of:

$(El_xAl_yP_z)O_2$ wherein El is an element selected from the group consisting of silicon, magnesium, zinc, iron, cobalt, nickel, manganese, chromium, and mixtures thereof, and where "x" is the mole fraction of El and has a value from 0.001 to about 0.5, "y" is the mole fraction of Al and has a value of at least 0.01, "z" is the mole fraction of P and has a value of at least 0.01, and x+y+z=1. Preferably, the El content on a mole fraction basis varies from about 0.005 to about 0.15, with a more preferred El content from about 0.005 to about 0.06 on a mole fraction basis and a preferred El is silicon.

When silicon is the preferred El the molecular sieve is referred to as a SAPO. SAPO's describe a broad group of molecular sieves that are used for a broad range of hydrocarbon processes. The particular SAPO of interest is SAPO-34, which in turn has a broad range of compositions. Currently, the production of SAPO-34 crystals produce crystals having a mix of structure, wherein the predominant structures are CHA framework and AEI framework. This mix of frameworks can be seen by the amount of intergrowths in the crystals. The present invention produces a SAPO-34 having an essentially pure chabazite, or CHA, structure, and is most useful in MTO processing. By increasing the amount of CHA versus AEI, i.e. substantially pure CHA, a SAPO-34 is produced that generates higher conversions and better selectivities to ethylene and propylene.

By controlling the range of reaction mixture composition, especially of the templating agent, smaller and more numerous crystals are formed. A preferred organic templating agent is tetraethylammonium hydroxide (TEAOH). It is preferred to form crystals having a crystal size less than 5 micrometers and more preferred to produce crystals of less than about one micrometer in size, to reduce mass transfer limitations and secondary reactions due to residence times in the pores. The crystal size can be determined by procedures known to persons skilled in the art. One method of determining crystal size is Scanning Electron Microscopy (SEM) of representative samples of crystals. The process of the present invention produces crystals sized preferably less than 1 micrometer.

Molecular sieves of this invention have predominantly a rhombohedral crystal morphology or a three-dimensional branched morphology with thick branched plates. However, the crystals have angles between the faces that are close to 90 degrees, such that the structure is almost cubic, or pseudo-cubic. By the term "pseudo-cubic", it is meant not only crystals in which all the dimensions are the same, but also those in which the aspect ratio is less than or equal to 2. It is also necessary that the average smallest crystal dimension be at least 50 nanometers and preferably at least 100 nanometers. Without being bound by any one particular theory, it appears that a minimum thickness is required so that the diffusion path for desorption of ethylene and propylene is sufficiently long to allow differentiation of the two molecules.

The molecular sieves of the present invention may be combined with one or more formulating agents, to form a molecular sieve catalyst composition or a formulated molecular sieve catalyst composition. The formulating agents may be one or more materials selected from the group consisting of binding agents, matrix or filler materials, catalytically active materials and mixtures thereof. This formulated molecular sieve catalyst composition is formed into desired shapes and sized particles by well-known techniques such as spray drying, pelletizing, extrusion, and the like.

The molecular sieve of the present invention may be combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and in controlling the rate of conversion in a particular process. Matrix materials include synthetic and naturally occurring materials such as clays, silica, and metal oxides. Clays include, but are not limited to, kaolin, kaolinite, montmorillonite, saponite, and bentonite.

Upon combining the molecular sieve and the matrix material, optionally with a binder, in a liquid to form a slurry, mixing, preferably rigorous mixing is needed to produce a substantially homogeneous mixture containing the molecular sieve. Binders include any inorganic oxide well known in the art, and examples include, but are not limited to, alumina, silica, aluminum-phosphate, silica-alumina, and mixtures thereof. When a binder is used, the amount of molecular sieve present is in an amount from about 10 to 90 weight percent of the catalyst. Preferably, the amount of molecular sieve present is in an amount from about 30 to 70 weight percent of the catalyst. Non-limiting examples of suitable liquids include one or a combination of water, alcohol, ketones, aldehydes, and/or esters. The most preferred liquid is water.

The molecular sieve and matrix material, and the optional binder, may be in the same or different liquid, and may be combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles and/or sub-particle size distribution of the molecular sieve catalyst composition that is then fed to a forming unit that produces the molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition.

Generally, the size of the particles is controlled to some extent by the solids content of the slurry. However, control of the size of the catalyst composition and its spherical characteristics are controllable by varying the slurry feed properties and conditions of atomization. Also, although spray dryers produce a broad distribution of particle sizes, classifiers are normally used to separate the fines which can then be milled to a fine powder and recycled to the spray dryer feed mixture.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° to about 1000° C., preferably from about 500° to about 800° C., more preferably from about 550° C. to about 700° C., and most preferably from about 600° C. to about 700° C. Calcination is performed in an environment such as air, nitrogen, helium, flue gas (combustion product lean in oxygen), or any combination thereof. The heating is carried out for a period of time typically from 30 minutes to 15 hours, preferably from 1 hour to about 10 hours, more preferably from about 1 hour to about 5 hours, and most preferably from about 2 hours to about 4 hours. The calcination with air or oxygen removes both the fluoride and any of the organic template, including any occluded within the structure.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

One aspect of the present invention includes a process directed to the conversion of a feedstock comprising one or more oxygenates to one or more olefins. In the process of the invention, the feedstock contains one or more oxygenates, more specifically, one or more organic compounds containing at least one oxygen atom. In the most preferred embodiment of the process of the invention, the oxygenate in the feedstock is one or more alcohols, preferably aliphatic alcohols where the aliphatic moiety of the alcohols has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

In the present invention, the feedstock comprising one or more oxygenates, preferably an alcohol such as methanol, is converted in the presence of the molecular sieve formed from the present process, into an olefin having from 2 to 6 carbon atoms, preferably olefins having 2 to 4 carbons atoms, and most preferably to ethylene and/or propylene.

In one embodiment of the process the amount of light olefin(s) produced, based on the total weight of hydrocarbon produced, is greater than 50 wt-%, preferably greater than 60 wt-%, more preferably greater than 70 wt-%.

A preferred process is the MTO process, wherein the feedstock has methanol as a primary constituent. The methanol is contacted with the catalyst at reaction conditions to produce a product stream containing primarily ethylene and propylene. While other catalysts, and other SAPO-34 catalysts can perform the same conversion, this improved catalyst generates a higher yield of olefins from methanol.

The feedstock may contain at least one diluent, typically used to reduce the concentration of the feedstock, which is generally non-reactive in the process. Examples of diluents include helium, argon, nitrogen, carbon monoxide, carbon dioxide, water (steam), essentially non-reactive paraffins (especially alkanes such as methane, ethane, and propane), essentially non-reactive aromatic compounds, and mixtures thereof. The most preferred diluents are water and nitrogen, with water being particularly preferred. The diluent may be present in the feedstock in an amount between about 1 and about 99 mol-% based on the total number of moles of all feed components fed to the reaction zone (or catalyst).

Water, is used either in a liquid or a vapor form, or a combination thereof. The diluent is either added directly to a feedstock entering into a reactor or added directly into a reactor. In one embodiment, the amount of diluent in the feedstock is in the range from about 1 to about 99 mol-% based on the total number of moles of the feedstock and diluent, preferably from about 1 to 80 mol-%, more preferably from about 5 to about 50 mol-%, most preferably from about 5 to about 25 mol-%.

The process can be carried out as a fixed bed process or a fluidized bed process (including a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, fast-fluidized bed reactors, and the like. Suitable reactor types are described in for example U.S. Pat. No. 4,076,796; U.S. Pat. No. 6,287,522 B1; and U.S. Pat. No. 6,166,282 which are incorporated by reference in their entirety. In a preferred embodiment, the process includes a reactor system, a regeneration system, and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock is fed to the one or more riser reactor(s) in which a molecular sieve catalyst composition is introduced. In one embodiment, the molecular sieve catalyst composition is contacted with a liquid or gas, or combination thereof, prior to being introduced to the riser reactor(s), preferably the liquid is water or methanol, and the gas is an inert gas such as nitrogen.

The process of the invention is preferably carried out in the vapor phase such that the feedstock is contacted in a reaction zone with a silico-aluminophosphate molecular sieve at effective process conditions, i.e., an effective temperature, pressure, WHSV (weight hourly space velocity) and, optionally, an effective amount of diluent, correlated to produce light olefins. Alternatively, the process may be carried out in a liquid phase. When the process is carried out in the liquid phase, the process necessarily involves the separation of products formed in a liquid reaction media and can result in different conversions and selectivities of feedstock to product with respect to the relative ratios of the light olefin products as compared to that formed by the vapor phase process.

The temperature which can be employed in the process can vary over a wide range depending, usually between about 200° and about 700° C., preferably between about 250° and about 600° C., and most preferably between about 300° and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° and about 700° C.

The process is effectively carried out over a wide range of pressures including autogenous pressures. At pressures between about 100 Pa (0.001 atmospheres) and about 100 MPa (1000 atmospheres), light olefin products will not necessarily form at all pressures. The preferred pressure is between about 1 kPa (0.01 atmospheres) and about 10 MPa (100 atmospheres). The pressures referred to herein for the process are exclusive of the inert diluent, if any is present, and refer to the partial pressure of the feedstock. Pressures outside the stated range are not excluded from the scope of this invention, although such do not fall within certain desirable embodiments of the invention. At the lower and upper end of the pressure range, light olefin products can be formed but the process will not be optimum.

The process is effectively carried out over a wide range of weight hourly space velocity (WHSV) for the feedstock and is generally between about 0.01 and about 100 $hr^{-1}$ and preferably between about 0.1 and about 40 $hr^{-1}$. Values above 100 $hr^{-1}$ may be employed and are intended to be covered by the instant process, although such are not preferred.

It has been discovered that the addition of a diluent to the feedstock prior to such being employed in the instant process is generally beneficial, although not required. The instant process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such silico-aluminophosphate molecular sieves in series to provide for a desired product mixture. Owing to the nature of the process, it may be desirous to carry out the instant process by use of the silico-aluminophosphates in a dynamic (e.g., fluidized or moving) bed system or any system of a variety of transport beds rather than in a fixed bed system. Such systems would readily provide for any regeneration (if required) of the silico-aluminophosphate molecular sieve catalyst after a given period of time. If regeneration is required, the silico-aluminophosphate molecular sieve catalyst can be continuously introduced as a moving bed to a regeneration zone where it can be regenerated, such as, for example, by removing carbonaceous materials by oxidation in an oxygen-containing atmosphere. In the preferred practice of the invention, the catalyst will be subject to a regeneration step by burning off carbonaceous deposits accumulated during reactions.

In an embodiment, the amount of fresh liquid feedstock fed separately or jointly with a vapor feedstock, to a reactor system is in the range of from 0.1 to about 85 wt-%, preferably from about 1 to about 75 wt-%, more preferably from about 5 to about 65 wt-% based on the total weight of the feedstock including any diluent contained therein. The liquid and vapor feedstocks are preferably the same composition, or contain varying proportions of the same or different feedstock with the same or different diluent.

EXAMPLES

A series of molecular sieves were prepared as described below. A gel composition was formed having a ratio of alumina ($Al_2O_3$) to phosphate ($P_2O_5$) to TEAOH of approximately 1 to 1 to 1 on a molar basis. The gel was formed with water in an amount sufficient to provide a ratio of approximately 40 to 1 of water to alumina on a molar basis. To this gel, a fluoride compound was added in an amount sufficient to provide a ratio of approximately 0.5-1 to 1 of fluoride to alumina on a molar basis, and silica ($SiO_2$) was added in amounts between 0 and 2 times the amount of alumina on a molar basis. This provided a gel composition of:

1TEAOH.$x$SiO$_2$.Al$_2$O$_3$.P$_2$O$_5$.40H$_2$O.$y$HF where x is from 0.001 to 2 and y is from 0.2 to 1. After forming the mixture, the gel was placed in a sealed vessel and heated to about 175° C. The gels were heated for about 48 hours at 175° C. and at an autogenous pressure. The samples of SAPO-34 produced with this procedure were analyzed and the products of the as synthesized SAPO-34 show that the framework silicon content ranged from a mole fraction of about 0 to about 0.26, as seen in Table 1. The Al mole fractions in excess of 0.5 are believed to be due to the presence of non-framework Al as alumina debris, and this is supported by TEM and SEM observations. Samples of the crystals formed from this procedure were analyzed by X-ray diffraction. The samples show unit cells that index as triclinic due to framework distortion from fluoride bonded to framework Al. The fluoride prevents AEI formation and there is little or no CHA/AEI intergrowth visible from the spectra.

The samples were further calcined in air at about 600° C. to removed both the fluoride and the occluded organic material. The calcination allowed the framework to relax to the more symmetrical hexagonal unit cell typical of the CHA framework type. FIG. 1 shows the change in spectra for a sample as synthesized, and after calcinations.

TABLE 1

Elemental analyses, on a molar basis, of as-synthesized SAPO-34 made in F-media with a TEAOH template.

| Sample ID | Aluminum | Phosphorus | Silicon | F |
|---|---|---|---|---|
| 1 | 0.49 | 0.510 | 0 | 0.09 |
| 2 | 0.53 | 0.462 | 0.008 | NA |
| 3 | 0.489 | 0.496 | 0.016 | 0.091 |
| 4 | 0.526 | 0.464 | 0.01 | NA |
| 5 | 0.508 | 0.462 | 0.03 | 0.051 |
| 6 | 0.508 | 0.44 | 0.052 | 0.033 |
| 7 | 0.486 | 0.402 | 0.112 | 0.005 |
| 8 | 0.413 | 0.326 | 0.261 | 0.012 |

The elemental analyses show the presence of F in the as synthesized products. From the analyses, the amount of F increases as the Si content decreases, and there is a maximum content of F when the sample has no Si. Without being bound to any theory, it is believed that there is a balance between the framework Si and the occluded F in their shared role of balancing the positive charge on the template during the synthesis of the crystals.

The performance of the fluoride produced catalyst, F-SAPO-34, was compared with the standard SAPO-34 produced without fluoride. Testing the catalyst of the present invention shows that the totals of ethylene and propylene were significantly greater than that of the SAPO-34 with comparable silicon levels, but prepared under non-fluoride conditions, as shown in Table 2.

TABLE 2

MTO performance of selected SAPO-34

| Catalyst | Mol % Si | Ethylene | Propylene | Ethylene + propylene |
|---|---|---|---|---|
| F-SAPO-34 | 5 | 48.6 | 36.8 | 85.4 |
| SAPO-34 | 5 | 50.8 | 30.8 | 81.7 |

Improvement in the molecular sieve crystal structure by reducing, and substantially eliminating the intergrowths produces a molecular sieve that gives an improved selectivity of ethylene and propylene, and an increased ratio of propylene to ethylene, allowing for greater high value products produced from oxygenates.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:
1. A process for hydrocarbon conversion comprising:
contacting a feedstock in a reactor with a molecular sieve prepared according to a process for preparing a crystalline metallo-aluminophosphate molecular sieve having a framework composition on an anhydrous and calcined basis expressed by an empirical formula of

(El$_x$Al$_y$P$_z$)O$_2$, wherein El is selected from the group consisting of silicon, magnesium, zinc, iron, cobalt, nickel, manganese, chromium, and mixtures thereof, "x" is the mole fraction of El and has a value from 0.001 to about 0.5, "y" is the mole fraction of Al and has a value of at least 0.01, "z" is the mole fraction of P and has a value of at least 0.01 and x+y+z=1, the process comprising:

provide a reaction mixture comprising an aluminum source, a phosphorous source, water, an El source, an organic template source and a fluoride source to form a catalyst and wherein the template to phosphorus ratio on a molar basis is less than about 0.5; and crystallizing the molecular sieve at a temperature between about 100° C. and about 250° C., to provide the molecular sieve and then calcining in air, where the molecular sieve is characterized as having an essentially pure CHA framework with an average crystal size less than about 5 micrometers; and generating an effluent stream with conversion products;

drawing off the effluent stream from the reactor; and passing the effluent stream to a separation unit to generate a product stream.

2. The process of claim 1 wherein the feedstock comprises oxygenates.

3. The process of claim 2 wherein the feedstock is selected from the group consisting of methanol, ethanol, dimethyl ether, diethyl ether, and mixtures thereof.

4. The process of claim 1 wherein the conversion products comprise one or more olefins.

5. The process of claim 4 wherein the olefins are selected from the group consisting of ethylene, propylene, and mixtures thereof.

6. The process of claim 1 wherein the conversion conditions are a temperature of about 300° C. to about 600° C., a pressure of about 0 kPa to about 17200 kPa (250 psig) and a weight hourly space velocity of about 1 to about 100 $hr^{-1}$.

* * * * *